US008522384B2

(12) United States Patent
Leung

(10) Patent No.: US 8,522,384 B2
(45) Date of Patent: Sep. 3, 2013

(54) TOOTHBRUSH WITH FLUID JET ASSEMBLY

(75) Inventor: Anthony Kit Lun Leung, Hong Kong (CN)

(73) Assignee: Conair Corporation, Stamford, CT (US)

( * ) Notice: Subject to any disclaimer, the term of this patent is extended or adjusted under 35 U.S.C. 154(b) by 300 days.

(21) Appl. No.: 13/089,781

(22) Filed: Apr. 19, 2011

(65) Prior Publication Data
US 2012/0266396 A1   Oct. 25, 2012

(51) Int. Cl.
*A46B 11/02* (2006.01)
(52) U.S. Cl.
USPC .................................. 15/29; 433/80; 601/162
(58) Field of Classification Search
USPC .................. 15/29, 22.1, 22.2, 167.1; 433/80, 433/89, 82, 120; 601/162
See application file for complete search history.

(56) References Cited

U.S. PATENT DOCUMENTS

| | | | |
|---|---|---|---|
| 4,530,369 A | 7/1985 | Adams | |
| 5,088,145 A | 2/1992 | Whitefield | |
| 5,301,381 A | 4/1994 | Klupt | |
| 5,304,010 A | 4/1994 | Hsing-San | |
| 5,309,590 A | 5/1994 | Giuliani et al. | |
| 5,359,747 A | 11/1994 | Amakasu | |
| 5,378,153 A | 1/1995 | Giuliani et al. | |
| 5,406,664 A | 4/1995 | Hukuba | |
| D387,908 S | 12/1997 | Stützer et al. | |
| D388,252 S | 12/1997 | Stützer et al. | |
| RE35,941 E | 11/1998 | Stansbury, Jr. | |
| D411,769 S | 7/1999 | Wright | |
| 5,934,908 A | 8/1999 | Woog et al. | |
| 6,030,215 A | 2/2000 | Ellion et al. | |
| 6,047,429 A | 4/2000 | Wu | |
| 6,203,320 B1 | 3/2001 | Williams et al. | |
| 6,230,717 B1 | 5/2001 | Marx et al. | |
| D452,775 S | 1/2002 | Wright | |
| D453,996 S | 3/2002 | Kling et al. | |
| D457,726 S | 5/2002 | Tse | |
| D458,027 S | 6/2002 | Ferber et al. | |
| D458,028 S | 6/2002 | McCurrach | |
| 6,453,499 B1 | 9/2002 | Leuermann | |
| D470,660 S | 2/2003 | Schaber | |

(Continued)

OTHER PUBLICATIONS

US D480,212, 10/2003, Vu (withdrawn)

*Primary Examiner* — Shay Karls
(74) *Attorney, Agent, or Firm* — Carter, DeLuca, Farrell & Schmidt, LLP

(57) ABSTRACT

A powered toothbrush assembly (100) includes an outer housing (102, 104), a brush head (106) and a fluid nozzle (138) adjacent the brush head (106), an inner housing (122) disposed within the outer housing (102,104) and having a motor (130) which is in operative engagement with the brush head (106) to impart motion to the brush head (106) and a pump mechanism (134) disposed within the inner housing (122). The outer housing (102,104) and the inner housing (122) define a chamber (142) therebetween for accommodating a fluid. The pump mechanism (134) includes a pump housing (156) having a pump inlet (168) dimensioned to permit entry of the fluid from the chamber (142) and a pump outlet (172) for permitting exit of the fluid from the pump housing (156), a pump (170) for imparting energy to the fluid entering the pump inlet (168) and directing the fluid to the pump outlet (172) and a conduit (180) in fluid communication with the pump outlet (172) and the fluid nozzle (138) for directing the fluid to the fluid nozzle (138) for release under pressure therefrom.

11 Claims, 8 Drawing Sheets

(56) References Cited

U.S. PATENT DOCUMENTS

| | | |
|---|---|---|
| D474,026 S | 5/2003 | Wright |
| D475,529 S | 6/2003 | Wright et al. |
| D476,485 S | 7/2003 | Mulder et al. |
| D479,403 S | 9/2003 | Breit et al. |
| 6,689,078 B1 * | 2/2004 | Rehkemper et al. .......... 601/162 |
| D487,349 S | 3/2004 | Julian |
| D489,183 S | 5/2004 | Akahori et al. |
| 6,766,549 B2 | 7/2004 | Klupt |
| 6,766,824 B2 | 7/2004 | Taylor |
| D493,960 S | 8/2004 | Jimenez et al. |
| D500,207 S | 12/2004 | Jimenez et al. |
| 6,845,537 B2 | 1/2005 | Wong |
| 6,848,141 B2 | 2/2005 | Eliav et al. |
| 6,886,208 B2 | 5/2005 | Kemp et al. |
| 6,902,337 B1 * | 6/2005 | Kuo .......................... 401/188 R |
| 6,918,154 B2 | 7/2005 | Ben-Ari |
| D508,776 S | 8/2005 | Kling et al. |
| D515,815 S | 2/2006 | Jimenez et al. |
| D515,816 S | 2/2006 | Jimenez et al. |
| 7,080,980 B2 | 7/2006 | Klupt |
| D527,185 S | 8/2006 | Vu |
| 7,120,960 B2 | 10/2006 | Hilscher et al. |
| D563,674 S | 3/2008 | Beedham |
| 7,356,866 B2 | 4/2008 | Chan |
| 7,386,904 B2 | 6/2008 | Fattori |
| 7,401,373 B2 | 7/2008 | Tybinkowski et al. |
| 7,401,377 B2 | 7/2008 | Birk et al. |
| D577,198 S | 9/2008 | Jimenez et al. |
| D580,173 S | 11/2008 | Beedham |
| 7,469,440 B2 | 12/2008 | Boland et al. |
| D586,125 S | 2/2009 | Winkler et al. |
| 7,495,358 B2 | 2/2009 | Kobayashi et al. |
| 7,703,163 B2 | 4/2010 | Jimenez et al. |
| D619,368 S | 7/2010 | Toshima |
| 7,784,136 B2 | 8/2010 | Gatzemeyer et al. |
| D623,416 S | 9/2010 | St. Laurent |
| 7,857,623 B2 | 12/2010 | Grez |
| 7,877,832 B2 | 2/2011 | Reinbold |
| 7,877,833 B2 | 2/2011 | Gavney, Jr. |
| 8,393,817 B2 * | 3/2013 | Heil et al. .................. 401/188 R |
| 2005/0278878 A1 | 12/2005 | Liao et al. |
| 2006/0254007 A1 | 11/2006 | Banning |
| 2009/0070949 A1 | 3/2009 | Sagel et al. |
| 2009/0113643 A1 | 5/2009 | Tybinkowski et al. |
| 2009/0113648 A1 | 5/2009 | Vaynberg et al. |
| 2009/0119859 A1 | 5/2009 | Podolsky |
| 2009/0211042 A1 | 8/2009 | Bock |
| 2010/0263143 A1 | 10/2010 | Sorrentino |

* cited by examiner

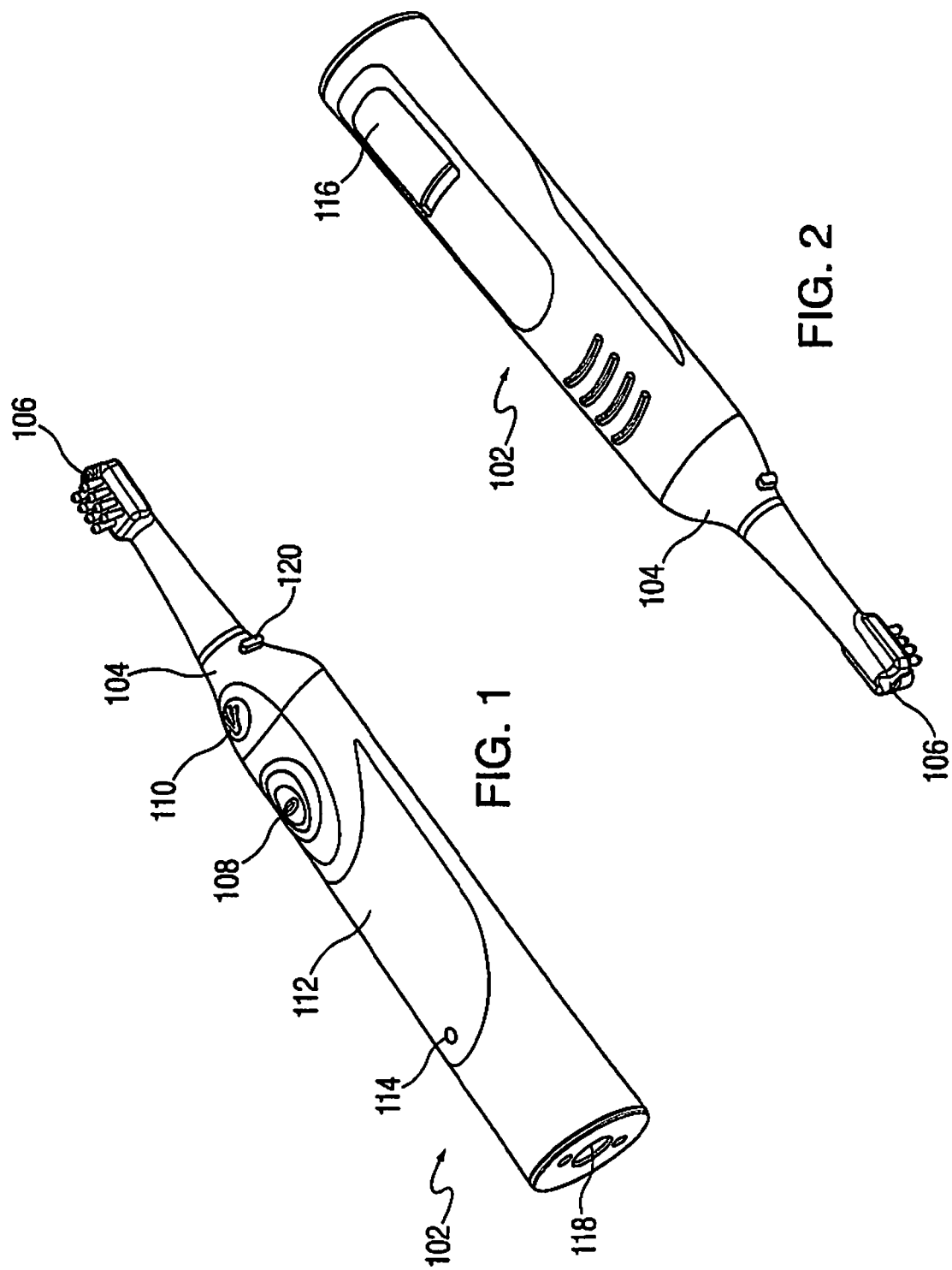

TOOTHBRUSH WITH FLUID JET ASSEMBLY

BACKGROUND

1. Technical Field

The present invention relates to a toothbrush, and, in particular, relates to an electric or battery operated toothbrush having fluid jet capabilities.

2. Background of the Related Art

Various toothbrush devices are commonly known in the art including manual toothbrushes and electrical/battery operated toothbrushes. Examples of such toothbrushes are disclosed in commonly assigned U.S. Pat. Nos. 6,735,804, 6,597,000 Des. 456,608 and Des. 457,000, the entire contents of each disclosure being incorporated by reference herein.

SUMMARY

Accordingly, the present invention relates to further improvements in electrical or battery operated toothbrush assemblies. In accordance with one embodiment of the present disclosure, a powered toothbrush assembly includes an outer housing, a brush head and a fluid nozzle adjacent the brush head, an inner housing disposed within the outer housing and having a motor which is in operative engagement with the brush head to impart motion to the brush head and a pump mechanism disposed within the inner housing. The outer housing and the inner housing define a chamber therebetween for accommodating a fluid. The pump mechanism includes a pump housing having a pump inlet dimensioned to permit entry of the fluid from the chamber and a pump outlet for permitting exit of the fluid from the pump housing, a pump for imparting energy to the fluid entering the pump inlet and directing the fluid to the pump outlet and a conduit in fluid communication with the pump outlet and the fluid nozzle for directing the fluid to the fluid nozzle for release under pressure therefrom.

The pump mechanism may be operable in a first mode of operation for directing air passing through an air inlet adjacent the pump housing and fluidly couplable with the conduit to the fluid nozzle and a second mode of operation for directing the fluid in liquid form contained within the chamber to the fluid nozzle.

A manually activated actuator may be mounted to the outer housing. The actuator is movable between a first condition corresponding to the first mode of operation of the pump mechanism and a second condition corresponding to the second mode of operation of the pump mechanism.

A drive mechanism may be associated with the pump mechanism. The drive mechanism is in operative engagement with the motor to impart motion to the brush head. The drive mechanism may includes a cam member in operative engagement with the motor, an elongated drive member operatively coupled to the cam member and adapted for reciprocal movement upon movement of the cam member, at least one drive gear operatively coupled to the drive member and adapted for reciprocal movement therewith and wherein the brush head includes a plurality of individual bristles. Each bristle may have a bristle gear adapted to cooperatively engage the at least one drive gear, whereby movement of the drive gears causes corresponding rotational movement of the bristle gears and the bristles.

The powered toothbrush may include a liquid check valve adjacent the pump outlet. The liquid check valve is dimensioned to prevent retrograde liquid flow. An air check valve may be adjacent the air inlet, and dimensioned to prevent liquid flow through the air inlet. A pressure valve may be in fluid communication with the fluid conduit and dimensioned to open upon achieving a predetermined pressure in the fluid conduit, to thereby permit release of the liquid into the fluid chamber.

A manually activated power switch may be provided to power the motor. A power source may be in electrical communication with the pump. The power source may include a rechargeable battery.

BRIEF DESCRIPTION OF THE DRAWINGS

Various embodiments of the present disclosure are described hereinbelow with references to the drawings, wherein:

FIGS. 1 and 2 are perspective views of the toothbrush with fluid jet assembly in accordance with the principles of the present invention;

DETAILED DESCRIPTION OF THE EMBODIMENTS

Figure 3:
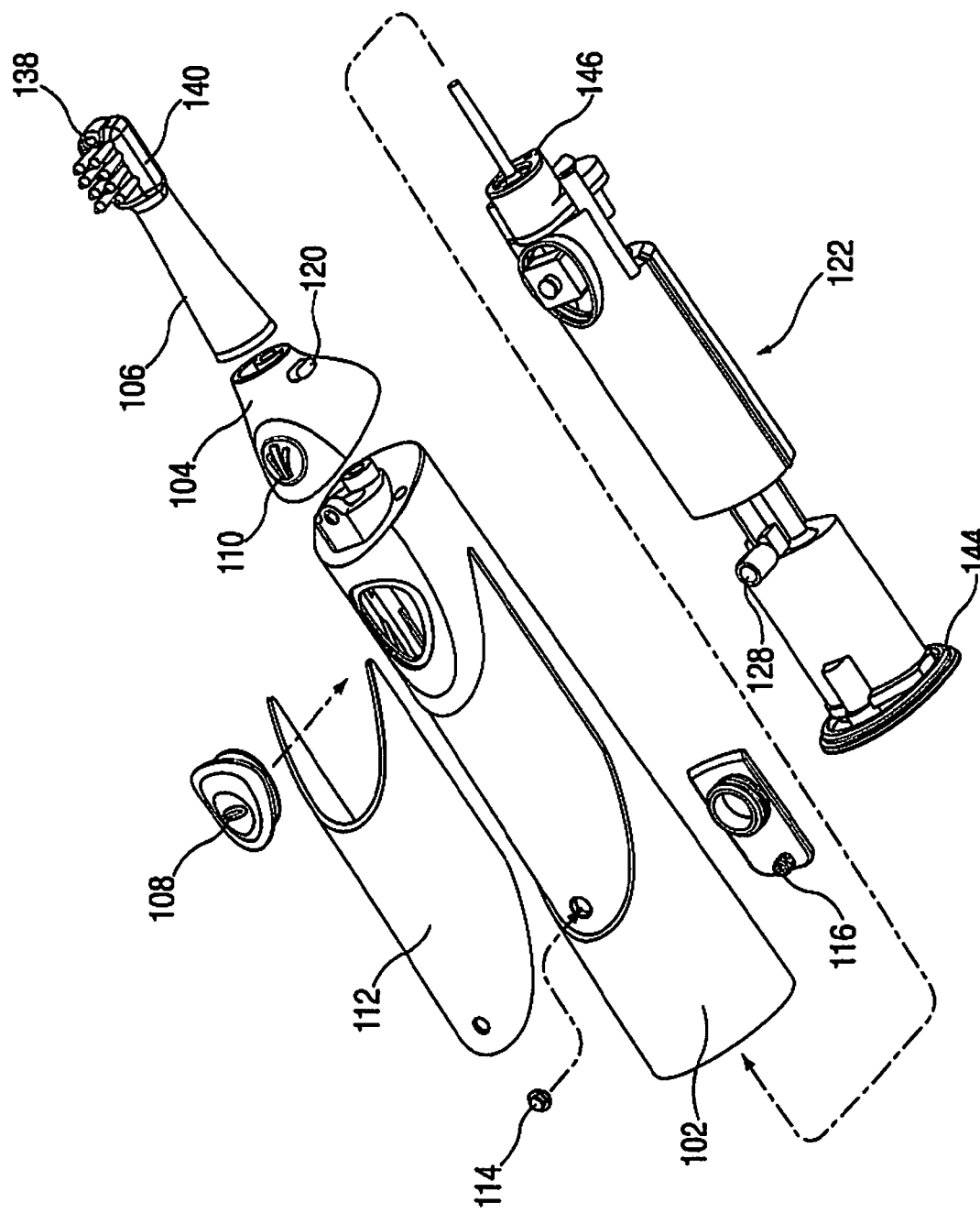
FIG. 3 is a perspective view with parts separated of the toothbrush assembly.
Figure 5:
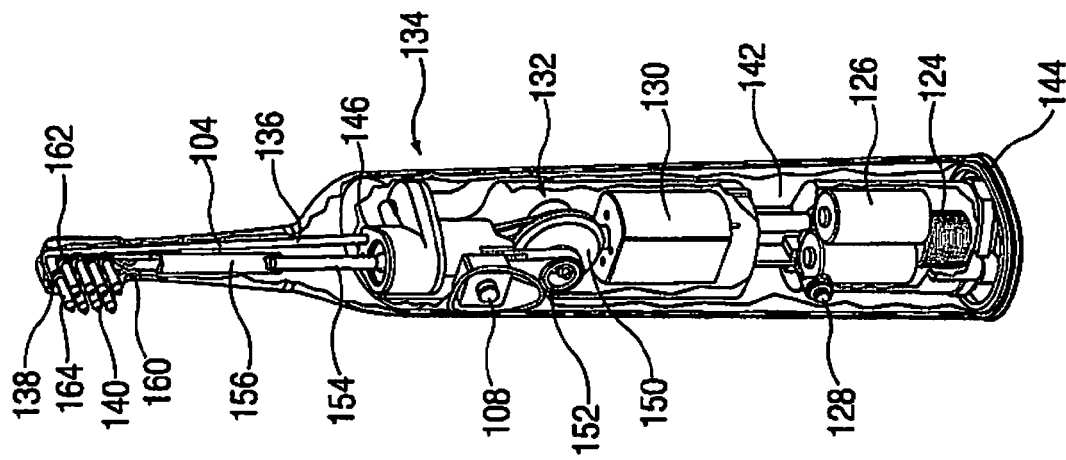
FIG. 5 is a perspective view with portions of the inner housing removed illustrating components of the motor and the drive mechanism.
Figure 4:
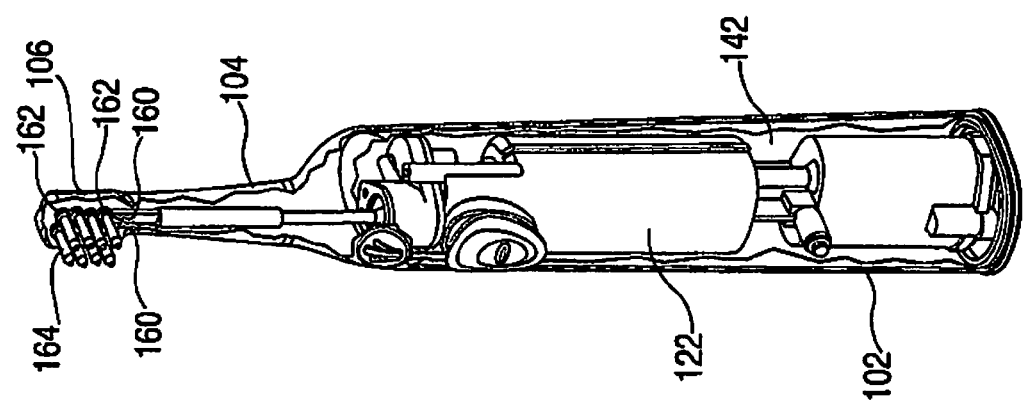
FIG. 4 is a perspective view with portions of the main housing removed illustrating the inner housing.

Referring now to the drawings wherein like reference numerals identify similar components throughout the several views, FIGS. 1-2 illustrate the toothbrush with fluid/water jet assembly in accordance with the principles of the present invention. Toothbrush assembly 100 is electrically or battery operated and has a driven bristle head with fluid jet capabilities for mouth cleansing and food particle removal.

With reference to FIG. 3, in conjunction with FIGS. 1-2, toothbrush assembly 100 includes outer main housing 102, top housing 104 coupled to the main housing 102 and brush head 106, these components constituting the outer housing of the toothbrush assembly 100. Although shown as separate units adapted for releasable connection to each other, main housing 102, top housing 104, and brush head 106 may be a single monolithic or integral housing unit. Toothbrush assembly 100 further includes a manually activated power or on/off switch 108 and a fluid jet or manually activated fluid actuator 110 with on/off capabilities.

The remaining external components of toothbrush assembly 100 include decorative cover 112 for mounting to main housing 102, light or LED cover 114 for enclosing a light mounted within main housing 102 and fluid or liquid tank cover 116. Fluid tank cover 116 is releasably mountable to main housing 102 and permits access to an internal fluid chamber to permit the operator to supply the fluid chamber with fluid. A socket 118 with electrical contacts is disposed on the lower surface of main housing 102. A release lock 120 is provided to permit release of the top housing 104 and/or brush head 106. The release lock 120 may be any known locking mechanism selected to releasably connect the components.

Referring now to FIGS. 3-6, the interior of toothbrush assembly 100 will be discussed. Toothbrush assembly 100 includes internal or inner housing 122 which is fluid proof or tight and accommodates the functional components of the toothbrush assembly 100. Inner housing 122 includes, or has mounted therein, induction charging coil 124, rechargeable battery 126 in electrical connection with the induction coil 124 and lamp or LED 128 which is exposed through a lens or cover within the inner housing 122. Inner housing 122 further encloses motor 130, a drive or cam mechanism 132, a pump mechanism 134 associated with the drive mechanism 132, a conduit 130 in fluid communication with the pump mechanism 134 and with a jet nozzle 138 disposed adjacent rotary bristle head 140. Motor 130 may be any dc motor suitable for its intended purpose of driving a small appliance, or may be an ac motor. The components of the drive mechanism 132 and the pump mechanism 134 will be discussed in detail hereinbelow.

Outer housing 102, 104 and inner housing 122 define an internal chamber 142 therebetween when assembled. Internal chamber 142 is for accommodating fluids, e.g., liquids having antiseptic qualities or the like, or even water, to be supplied to, and distributed by pump mechanism 134. Tank cover 116 permits access to internal chamber 142 to permit the operator to supply the chamber 142 with the desired fluid. Sealing rings or gaskets 144, 146 are disposed on the upper and lower areas of inner housing 122 and engage the internal wall of housings 102, 104 in sealed relation therewith to prevent ingress or egress of fluids relative to the internal chamber 142.

Figure 6:
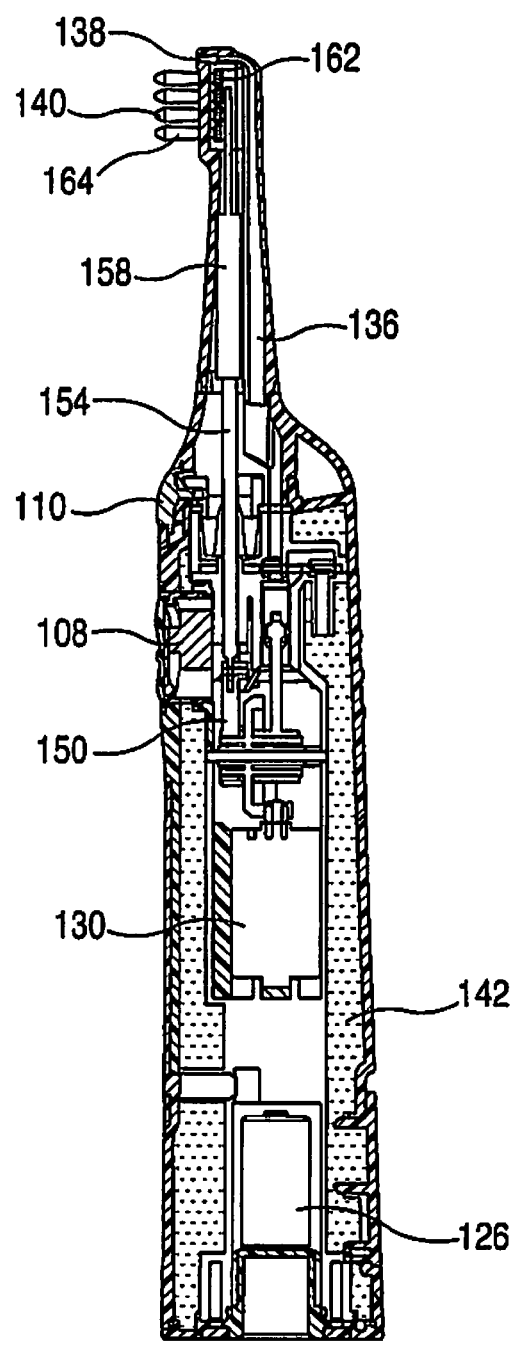
FIG. 6 is a side cross-sectional view of the toothbrush assembly.
Figure 8:
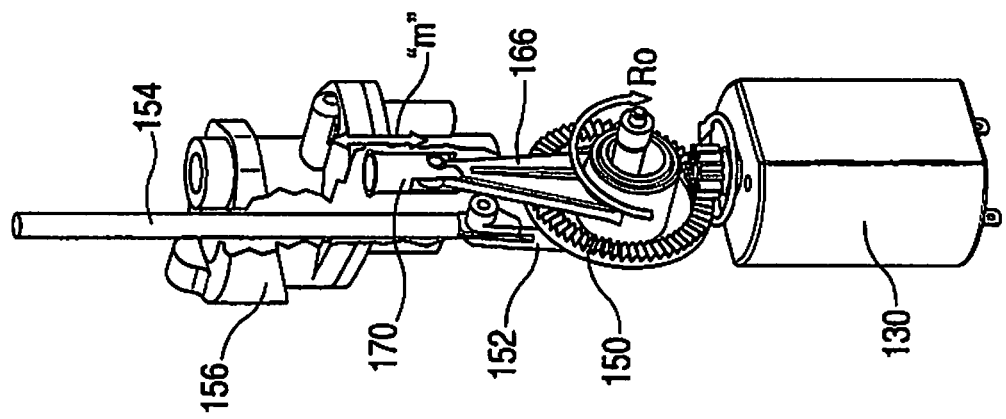
FIGS. 7 and 8 are perspective views of the drive and pump mechanisms of the toothbrush assembly.
Figure 7:
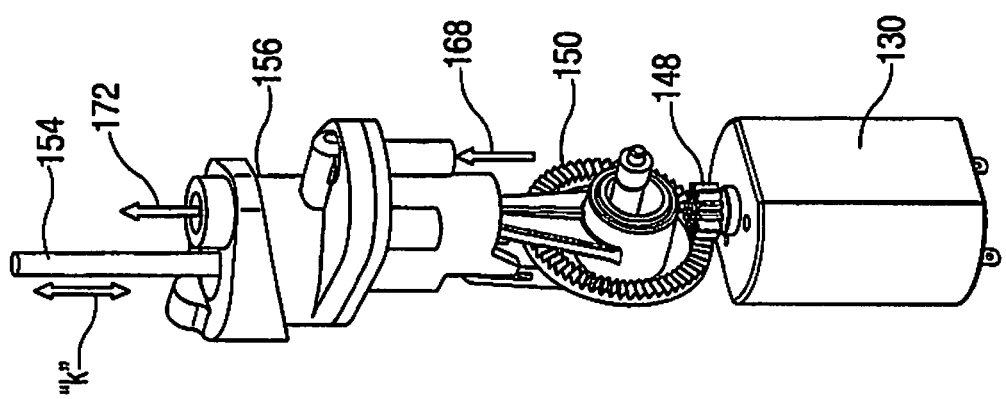

Referring now to FIGS. 7-8 in conjunction with FIG. 6, cam or drive mechanism 132 will be described. In one embodiment, drive mechanism 132 includes pinion gear 148 mounted to the output or spindle of motor 130, crown gear 150 in intermeshing relation with the pinion gear 148, and drive crank shaft 152 connected to crown gear 150. The longitudinal axis of the drive crank shaft 152 may be offset from the axis about which the crown gear 150 (e.g., an eccentric gear) rotates and may be connected to the crown gear 150 through an appropriate bearing or the like. Accordingly, rotational movement of pinion gear 148 occurring during operation of motor 130 will cause crown gear 150 to rotate, which, in turn effects drive crank shaft 152 to move in a reciprocal longitudinal motion (in the direction of arrows "k") with respect to the axis of the crank shaft 152. Drive crank shaft 152 is connected to stainless steel actuator rod 154 which extends through an opening in water pump housing 156.

Referring again to FIGS. 5-7, actuator rod 154 may be connected to another rod element 158 (preferably, plastic) which extends within brush head 106. Rod element 158 preferably includes at least one or a pair of opposed racks 160 which interact with gears 162 attached to bristles 164. Reciprocal longitudinal movement of racks 160 during corresponding reciprocal longitudinal movement of rod element 158 causes gears 162 to rotate in corresponding clockwise and counterclockwise directional movements, which in turn, causes bristles 164 to also oscillate or rotate in similar manner.

Figure 10:
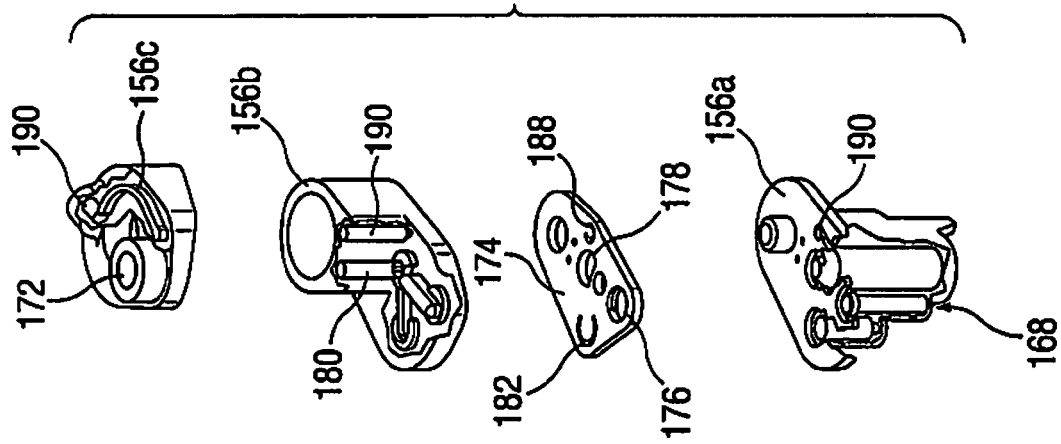
FIGS. 9 and 10 are perspective views of the water pump and associated components of the toothbrush assembly.
Figure 9:
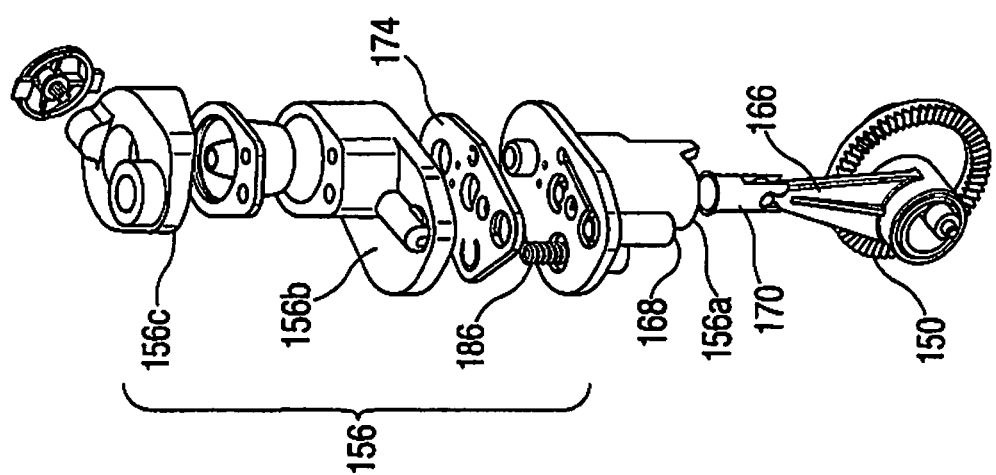

Referring to FIGS. 9-10, in conjunction with FIGS. 7-8, pump mechanism 134 will be discussed. Pump mechanism 134 includes pump housing 156 which at least partially receives water pump crank shaft 166. Pump housing 156 permits entry and exit of fluids from internal chamber 142. Specifically, pump housing 156 includes fluid inlet port 168 which is fluidly couplable with internal chamber 142 to permit entry and passage of fluid during activation of pump mechanism 134. Within pump housing 156 and attached to pump crank shaft 166 is pump or piston 170 which drives the fluid through fluid outlet port 172 during operation of the pump mechanism 156.

Pump mechanism 134 is actuated through motor 130 which drives crown gear 150 as discussed hereinabove. The longitudinal axis of the pump crank shaft 166 may be offset from the axis about which the crown gear 150 rotates and may be connected to the crown gear 150 through an appropriate bearing or the like. Accordingly, rotational movement of crown gear 150 will effect pump crank shaft 166 to move in a reciprocal longitudinal motion (in the direction of arrows "m") with respect to the axis of the pump crank shaft 166. Piston 170 may be pivotally coupled to pump crank shaft 166 and will maintain its vertical orientation through its confinement within pump housing 156, but will oscillate in an up/down direction during movement of the pump crank shaft 166. In general, movement of piston 170 will drive the fluid received within fluid inlet port 168 from internal chamber 142 through fluid outlet port 172.

Referring now to FIGS. 9-10, further details of pump mechanism 134 will be discussed. Pump mechanism 134 includes a plurality of valves or checks to ensure proper operation of the pump mechanism 134 and/or of the toothbrush assembly 100. In one embodiment, pump housing 156 includes a number of housing components which accommodate various valves or checks to ensure appropriate delivery of fluids and to prevent the potential buildup of fluid pressure which may otherwise have a detrimental effect on the motor and its components. Pump housing 156 includes top, middle and bottom housings 156a, 156b, 156c, which are assembled together to form a single unit. A valve and sealing member 174 is mounted between bottom and middle housings 156c, 156b. Valve and sealing member 174 may be a gasket member or the like and may be fabricated from a suitable elastomeric material or any other suitable material. Valve and sealing member 174 includes a plurality of slits, openings or apertures which may be dimensioned and adapted to function as valves (e.g., to open, close or partially open) in response to pressure (e.g., both, positive or negative). In one embodiment, valve and sealing member 174 includes water inlet valve 176 adjacent or in line with fluid inlet port 168, check valve 178 adjacent to or in line with fluid conduit 180 of fluid exit port 172 of the pump housing 156 and over pressure valve 182 for opening in the event a blockage exists within fluid conduit 136 leading to jet nozzle 138 or within the jet nozzle 138 itself. Upon opening of the over pressure valve 182 fluid will be deposited back into internal chamber 142. Over pressure valve 182 may be controlled via spring 186, which engages the lower surface of the valve 182. The constant force of spring 186 may be selected to permit release of valve 182 when a predetermined pressure is achieved within fluid conduit 136. The threshold level is chosen to avoid pressure build up and potential damage to the component parts. A check valve 188 is in fluid communication with the air intake channel or conduit 190 within each of pump housings 156a, 156b, 156c.

Figure 11:
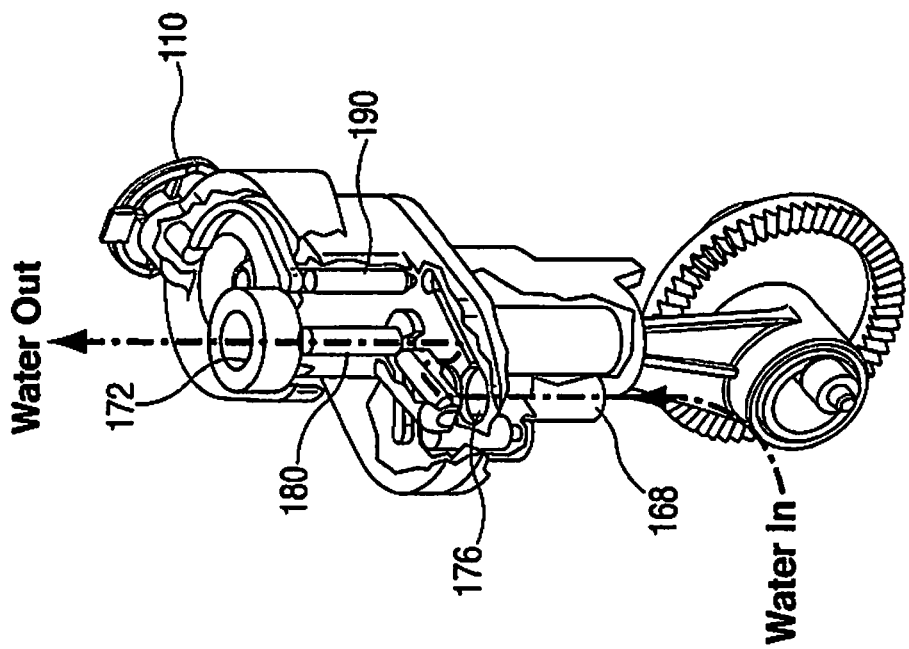
FIGS. 11-13 are views of the water pump illustrating stages of operation of the toothbrush assembly.
Figure 12:
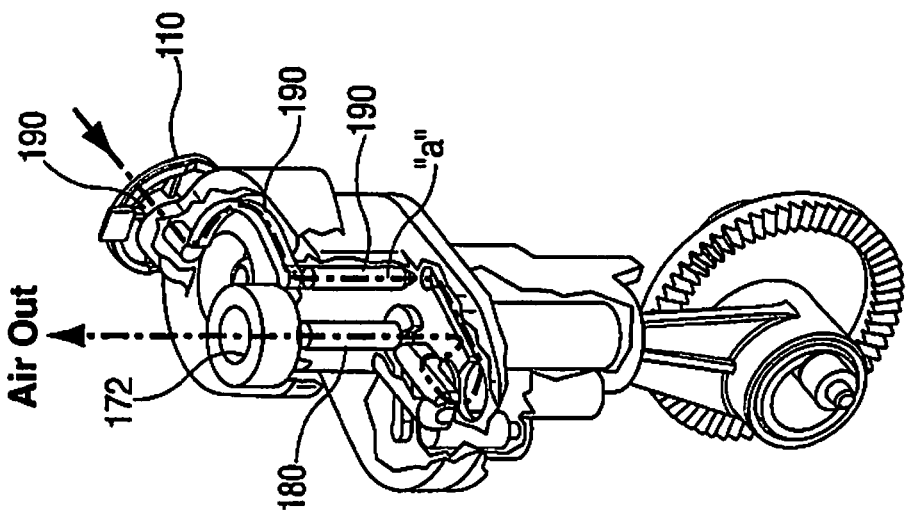
Figure 13:
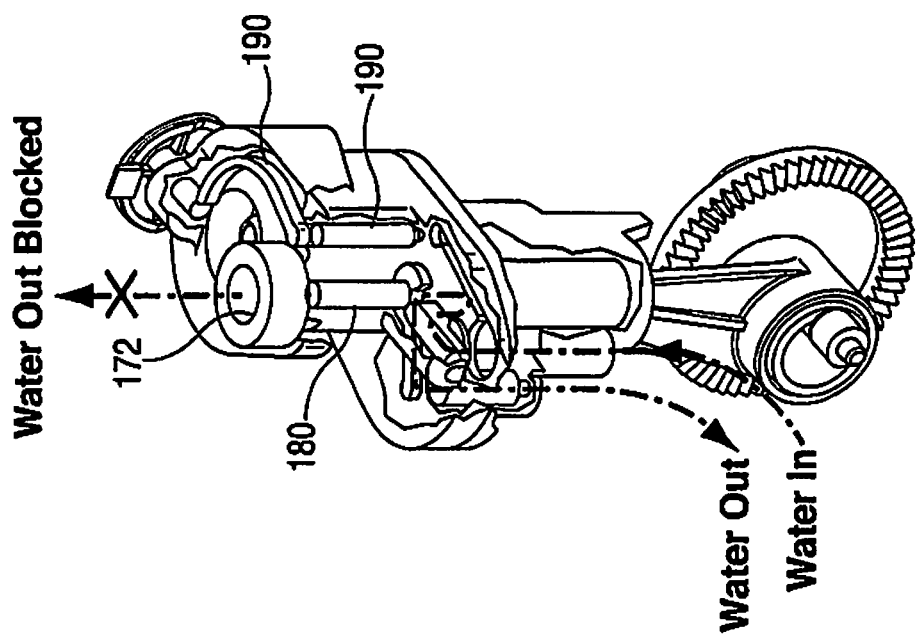

Operation of the toothbrush assembly 100 will now be discussed. With reference to FIG. 11, in a first mode of operation with the power on via actuation of switch 108 and fluid actuator 110 in the off position essentially maintaining air intake channel 190 in the open position as depicted in FIG. 11, air will flow through pump mechanism 134 along path "a" and exit fluid outlet port 172 for dispensing through fluid conduit 136 and out jet nozzle 138. Simultaneously therewith, drive mechanism 132 will be actuated to rotate bristles 164 in the aforedescribed manner. In the second stage of operation depicted in FIG. 12, fluid actuator 110 is depressed or activated, which closes air intake channel 190. Thus, fluid or liquid is received from internal chamber 142 within fluid inlet port 168, passing through water inlet valve 176 (FIG. 10) which opens to permit passage of the fluid into the pump housing 134 through fluid channel or conduit 180 and out fluid exit port 172 of the pump housing 156. The fluid path is identified by arrow "f". The fluid is pumped under pressure via piston 170 and through conduit 130 to exit jet nozzle 138 in bristle head 140. In this capacity, the jet nozzle 138 may be used to provide additional cleansing capacities or remove debris from the teeth. During the second stage of operation, check valve 178 prevents retrograde movement of the fluid back into the internal chamber 142. Also, during this stage or phase of the operation, the fluid is prevented from entering air channel 190 by way of air check valve 188. During operation, in the event there is blockage within jet nozzle 138 or fluid conduit 136, pressure valve 182 may be activated or released against spring 186 to permit exit of the fluids back into the internal chamber 142, thereby minimizing the potential of increased pressure in the pump mechanism 134, which, may otherwise damage the components of the pump. Pressure valve 182 may be spring activated having spring 186 dimensioned to release or compress upon achieving a predetermined pressure within conduit 136.

As indicated hereinabove, the various check valves may be slit, gasket zero closure valves adapted to open or close in response to pressure differential. Valves may be defined within an elastomeric component or may be incorporated as an integral component in check valve.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A powered toothbrush assembly, which comprises:
   an outer housing;
   a brush head and a fluid nozzle adjacent the brush head;
   an inner housing disposed within at least the outer housing, the inner housing including a motor, the motor in operative engagement with the brush head to impart motion to the brush head;
   the outer housing and the inner housing defining a chamber therebetween for accommodating a fluid;
   a pump mechanism disposed within the inner housing, the pump mechanism including:
      a pump housing having a pump inlet dimensioned to permit entry of the fluid from the chamber and a pump outlet for permitting exit of the fluid from the pump housing;
      a pump for imparting energy to the fluid entering the pump inlet and directing the fluid to the pump outlet; and
      a conduit in fluid communication with the pump outlet and the fluid nozzle for directing the fluid to the fluid nozzle for release under pressure therefrom.

2. The powered toothbrush assembly according to claim 1 wherein the pump mechanism is operable in a first mode of operation for directing air passing through an air inlet adjacent the pump housing and fluidly couplable with the conduit to the fluid nozzle and a second mode of operation for delivering the fluid in liquid form contained within the chamber to the fluid nozzle.

3. The powered toothbrush according to claim 2 including a manually activated actuator mounted to the outer housing, the actuator movable between a first condition corresponding to the first mode of operation of the pump mechanism and a second condition corresponding to the second mode of operation of the pump mechanism.

4. The powered toothbrush according to claim 3 including a liquid check valve adjacent the pump outlet, the liquid check valve dimensioned to prevent retrograde liquid flow.

5. The powered toothbrush according to claim 3 including an air check valve adjacent the air inlet, the air check valve dimensioned to prevent liquid flow through the air inlet.

6. The powered toothbrush according to claim 3 including a pressure valve in fluid communication with the fluid conduit, the pressure valve dimensioned to open upon achieving a predetermined pressure in the fluid conduit, to thereby permit release of the liquid into the fluid chamber.

7. The powered toothbrush according to claim 3 including a manually activated power switch, the power switch operable between on and off positions.

8. The powered toothbrush according to claim 7 including a power source in electrical communication with the pump.

9. The powered toothbrush according to claim 8 wherein the power source includes a rechargeable battery.

10. The powered toothbrush according to claim 1 including a drive mechanism associated with the pump mechanism, the drive mechanism in operative engagement with the motor to impart motion to the brush head.

11. The powered toothbrush according to claim 10 wherein the drive mechanism includes:
    a cam member in operative engagement with the motor;
    an elongated drive member operatively coupled to the cam member, the elongate drive member adapted for reciprocal movement upon movement of the cam member;
    at least one drive gear operatively coupled to the drive member and adapted for reciprocal movement therewith; and
    wherein the brush head includes a plurality of individual bristles, each bristle having a bristle gear adapted to cooperatively engage the at least one drive gear, whereby movement of the drive gears causes corresponding rotational movement of the bristle gears and the bristles.

* * * * *